United States Patent
Paufique

(10) Patent No.: US 11,241,469 B2
(45) Date of Patent: Feb. 8, 2022

(54) **ACTIVE INGREDIENT OBTAINED FROM *CALENDULA OFFICINALIS* AND USE IN THE PREVENTION AND TREATMENT OF CUTANEOUS MANIFESTATIONS DUE TO AN IMBALANCE IN THE EPIGENOME IN SKIN CELLS**

(71) Applicant: SOCIETE INDUSTRIELLE LIMOUSINE D'APPLICATION BIOLOGIQUE, Objat (FR)

(72) Inventor: Jean Paufique, Objat (FR)

(73) Assignee: SOCIETE INDUSTRIELLE LIMOUSINE D'APPLICATION BIOLOGIQUE, Objat (FR)

( * ) Notice: Subject to any disclaimer, the term of this patent is extended or adjusted under 35 U.S.C. 154(b) by 1183 days.

(21) Appl. No.: 14/843,236

(22) Filed: Sep. 2, 2015

(65) Prior Publication Data

US 2016/0074455 A1  Mar. 17, 2016

(30) Foreign Application Priority Data

Sep. 5, 2014 (FR) .................................. 14 58348

(51) Int. Cl.
*A61K 36/28* (2006.01)
*A61Q 19/08* (2006.01)
*A61K 8/9789* (2017.01)
*A61K 9/00* (2006.01)
*A61Q 19/00* (2006.01)

(52) U.S. Cl.
CPC ............ *A61K 36/28* (2013.01); *A61K 8/9789* (2017.08); *A61K 9/0014* (2013.01); *A61Q 19/00* (2013.01); *A61Q 19/08* (2013.01)

(58) Field of Classification Search
CPC ..................................................... A61K 36/28
USPC ......................................................... 424/764
See application file for complete search history.

(56) References Cited

U.S. PATENT DOCUMENTS

| 6,262,284 | B1* | 7/2001 | Khachik | ............... C07C 403/24 554/13 |
| 2006/0147397 | A1* | 7/2006 | Uehara | ................ A61K 8/0212 424/62 |
| 2013/0066117 | A1* | 3/2013 | Joseph | .................... C09B 61/00 568/816 |

FOREIGN PATENT DOCUMENTS

| FR | 2902334 A | 12/2007 |
| WO | 2012/085491 A1 | 6/2012 |

OTHER PUBLICATIONS

Zorn et al. "Enzymatic hydrolysis of carotenoid esters of marifold flowers and red paprika by commercial lipases and Pleurotus sapidus extraceular lipase", Enzyme and Microbial Technology 32 (2003) 623-628. (Year: 2003).*
Barreteau et al. "Production of Oligosaccharides as Promising New Food Additive Generation", H. Barreteau et al.: Oligosaccharides as Food Additives, Food Technol. Biotechnol. 44 (3) 323-333 (Year: 2006).*
Zorn et al. "Enzymatic hydrolysis of carotenoid esters of marigold flowers and red paprika by commercial lipases and Pleurotus sapidus extraceular lipase", Enzyme and Microbial Technology 32 (2003) 623-628. (Year: 2003).*
Annmarie Skin Care (https://www.annmariegianni.com/author/admin/) (Year: 2012).*
Chushenko, V. et al., "Carbohydrates of the Inflorescences of Calendula officinalis", Chemistry of Natural Compounds, Jul. 1, 1988 (Jul. 1, 1988), pp. 499-500, XP55178875, URL:http://rd.springer.com/content/pdf/10.1007/8F00598542.pdf.
A P Korzh et al: "Medicinal Plants Composition of Water-Soluble Polysaccharides From *Calendula officinalis* L. Flowers", Pharmaceutical Chemistry Journal, vol. 46, Jan. 1, 2012 (Jan. 1, 2012), pp. 23-25, XP55178594.

* cited by examiner

*Primary Examiner* — Michael Barker
*Assistant Examiner* — Deborah A Davis
(74) *Attorney, Agent, or Firm* — Nixon & Vanderhye

(57) ABSTRACT

The use of an active ingredient obtained from *Calendula officinalis* flowers as a product with topical application on the skin in the prevention or treatment of cutaneous manifestations caused by an imbalance of the epigenome in skin cells. Also, a hydrolyzate of *Calendula officinalis* flowers including oligosaccharides with a degree of polymerization of between 2 and 10, of fructose and glucose, with the compositions including it, and a cosmetic skin-care process.

13 Claims, No Drawings

ACTIVE INGREDIENT OBTAINED FROM *CALENDULA OFFICINALIS* AND USE IN THE PREVENTION AND TREATMENT OF CUTANEOUS MANIFESTATIONS DUE TO AN IMBALANCE IN THE EPIGENOME IN SKIN CELLS

This invention relates to the use of an active ingredient that is obtained from *Calendula officinalis* in the prevention and treatment of cutaneous manifestations due to an imbalance of the epigenome in skin cells.

The object of the invention is also a particular hydrolyzate of *Calendula officinalis*, the compositions comprising this hydrolyzate, and a cosmetic skin-care process comprising the topical application of such a composition.

Epigenetics is a science that is defined as the set of hereditary modifications in the function of genes that is not due to a modification of the DNA sequence. Actually, the epigenome, under the influence of the environment (such as pollution, stress, food, tobacco, and climate), conditions the expression of genes and manages the genetic information. For this purpose, the organism makes use of multiple mechanisms, among which are: the methylation of DNA, the modification of histones, and the expression of non-coding RNA such as the RNA "miRNA." Owing to the installation of these mechanisms, the cell is capable of adapting to its environment and thus of increasing its longevity.

The imbalances of these mechanisms and the modifications of the epigenome are consequently involved in numerous manifestations. In particular, the epigenetics was recently identified as a major element contributing to aging.

The objective of the invention is to propose a product that is suitable for use on the skin and is capable of boosting the epigenome and of acting on epigenetic mechanisms for preventing and combating the cutaneous manifestations caused by an imbalance of the epigenome in skin cells.

For this purpose, the object of the invention is the use of an active ingredient obtained from *Calendula officinalis* flowers.

*Calendula officinalis*, also known under the name of marigold, is a plant of the Aster family (Asteraceae), originally from Macaronesia (the Canary Islands, Madeira, Azores, Cape Verde), which today is for the most part cultivated in the countries of the Mediterranean area. It is known for its antibacterial, anti-inflammatory, and healing properties, and it is used in the food, medical and cosmetic fields. Traditionally, the marigold flowers are used internally for treating minor inflammations of the mouth and throat as well as externally for treating inflammations of the skin and for helping in healing minor wounds. In addition, various extracts of this plant have been developed for cosmetic applications. In particular, there are extracts that are rich in polyphenols and primarily in rutin that have anti-radical, anti-glycation, antioxidant, and consequently anti-aging cosmetic effectiveness.

Surprisingly enough, when applied on the skin, an active ingredient that is obtained from *Calendula officinalis* flowers has effects on the epigenetic mechanisms and boosts the epigenome of the cutaneous cells.

It can thus be used to boost the epigenome in the skin cells, in particular for preventing or combating the cutaneous manifestations linked to an imbalance of the epigenome in the skin cells. Advantageously, its action boosting the epigenome makes it possible in particular to combat the deleterious effects of cutaneous aging and in particular to increase the elasticity and tone of the skin, to smooth the microrelief, to improve the homogeneity, and the surface grain of the skin, and to impart a more youthful appearance.

The invention also has as its object a particular active ingredient, namely a hydrolyzate of *Calendula officinalis* flowers, comprising oligosaccharides with a degree of polymerization of between 2 and 10, consisting of fructose and glucose.

This hydrolyzate can be integrated into compositions that are suitable for a topical application on the skin, in particular compositions that comprise at least 0.5% of the hydrolyzate according to the invention. These compositions can be used for implementing a cosmetic skin-care process.

Other characteristics and advantages will emerge from the following detailed description of the invention.

The invention therefore has as its object an active ingredient that is obtained from *Calendula officinalis* flowers for its use as a product for topical application on the skin in the prevention or treatment of cutaneous manifestations caused by an imbalance of the epigenome in skin cells.

Active ingredient is defined as a set of multiple molecules obtained from *Calendula officinalis* flowers (extracted or obtained by transformation of the raw material, for example by hydrolysis) having an effect on the skin cells.

Epigenetics involves numerous mechanisms, among which are the methylation of DNA, the modification of histones, and the non-coding RNA.

The methylation of DNA is a stable modification and constitutes a transferable component in epigenetic regulation. This modification is essential for the development of the organism. It corresponds to the addition of a methyl group on the level of the cytosines that are present in the DNA and more particularly in areas called CpG islands. These CpG nucleotides are highly concentrated in the gene-promoting regions. Thus, after methylation of these residues, transcription is inhibited.

The modification of histones is a mechanism that is associated with the activation or the repression of gene expression. Actually, the histones are proteins that regulate the compaction of DNA and close off its accessibility. The DNA molecule winds around histones that themselves are arranged and folded up into chains of beads so as to form a fiber: chromatin. It consists of nucleosomes: protein octamer consisting of two copies of histones H2A, H2B, H3 and H4, around which the DNA molecule winds. Reading a gene requires the opening of the chromatin so as to allow access to the bare structure of the DNA. Thus, cycles of compaction/decompaction are enacted, or the histones exert the function of locks. They condition access of the cellular machinery to DNA. Without their initiator signal, the chromatin cannot be opened, and DNA cannot be translated into protein. So as to regulate the compaction of the chromatin, the histones undergo multiple modifications such as acetylation, methylation, ubiquitinylation or phosphorylation. These modifications target specific residues and are catalyzed by particular enzymes.

Thus, the chromatin can be functionally classified in two forms:
  The active chromatin or euchromatin that is characterized by an abundance of acetyl groups and a small proportion of methyl groups. This chromatin has a physical structure that is said to be open and accessible and is transcriptionally active.
  The inactive chromatin or heterochromatin that has marks opposite to euchromatin: few acetyl groups and an abundance of methyl groups. This chromatin is closed in a stable manner and silent.

These structures are highly dynamic, making possible the passage from one state to another. These gyrations are essential to the set-up of a process such as the transcription, the replication of DNA, and its repair. In response to physiological changes, the modification of histones modulates the structure of the chromatin and makes possible the adaptation of cellular functions.

During aging, a progressive deterioration of the stability of the chromatin and the gene expression is enacted. Multiple origins are possible: a maintenance defect of the telomeres but also the appearance of damage in the area of the DNA and the redistribution of heterochromatin focal points. Actually, aging is accompanied by the accumulation of genetic anomalies such as double-strand breaks. In response to this anomaly, H2AX (a variant of the histone H2) is phosphorylated into γH2AX and establishes a modification of the chromatin. These breaks result from the erosion of telomeres or else radical stress (UV, metabolic stress). They will activate a signaling of damage that can ultimately result in going into senescence. Actually, the senescent cells are characterized by an accumulation of the γH2AX focal points.

In contrast, senescence is associated with profound modifications of the chromatin structure that are reflected by an overall condensation and the formation of structures called heterochromatin foci associated with senescence (SAHF: Senescence Associated Heterochromatin Foci). These SAHF contain modifications of histones and proteins that are characteristic of a silent chromatin such as the histone H3 that is tri-methylated at lysine 9 (H3K9me3). These SAHF are described as inhibiting the expression of genes linked to the proliferation and contribute to stopping the growth that is associated with senescence. Furthermore, the methylation of the histones regulates the genes of the extracellular matrix and particularly the expression of COL1A1. The expression of this gene passes through a reduction of the methylation of the histone H3K9.

Advantageously according to the invention, an active ingredient that is obtained from the *Calendula officinalis* flowers applied to the skin limits the modifications of the chromatin by preventing the methylation of the lysine 9 of the histone H3 as well as the phosphorylation of the histone H2 in the cutaneous cells. In addition, it protects the chromatin from alterations induced by the environment by reducing the phosphorylation of the histone H2 and by preserving the procollagen.

By promoting the stability and the activity of the chromatin, it stabilizes and activates the synthesis of procollagen 1, a major protein of the extracellular matrix.

The object of the invention is therefore the use of an active ingredient obtained from *Calendula officinalis* flowers in the prevention or the treatment of cutaneous manifestations caused by a modification of the chromatin of the chromosomes of the skin cells.

Furthermore, it is known that the RNA can regulate genes. This effect passes through the non-coding RNA, molecules of less than 200 nucleotides that include miRNA, siRNA, piRNA, and snoRNA. Among these RNA, miRNA are in particular known for their involvement in aging.

The miRNA, small single-strand RNA, consist of 18 to 25 nucleotides. They result from a multi-stage cellular process initiated at the nuclear level with the production of a precursor: pre-miRNA. Under the action of multiple enzymatic complexes, this pri-miRNA gives rise to a mature miRNA that will:
  Inhibit the translation into protein,
  Or else bring about the cleavage of the target mRNA and its destruction.

These two degrees of regulation depend on the level of complementarity between the mRNA and the miRNA. The more significant the complementarity, the more mRNA will be degraded. In contrast, the miRNA being able to inhibit the protein translation despite an imperfect complementarity, they will be able to target multiple mRNA, and multiple miRNA will be able to regulate the same target. Numerous studies have shown that the level of the miRNA is modified with age and that these modifications can be at the origin of disorders.

By activating the miRNA expression, the cells will profoundly modify their capacities for synthesis. Actually, they constitute a regulating mechanism that controls the composition of the extracellular matrix but also the behavior of cells that reside there. The miRNA exert this effect by means of two mechanisms:
  Directly, by targeting the specific mRNA of the matrix;
  Indirectly, by modulating the expression of genes involved in the synthesis or the degradation of the latter.

Thus, about thirty miRNA have been able to be described for their involvement in the regulation of the extracellular matrix.

A study carried out by the applicant on miRNA (see tests of Item A.2) expressed by the SAHF fibroblasts made it possible to prove that the fibroblasts attacked under a solar simulator have a modified miRNA profile: the expression of 18 miRNA is increased while 7 miRNA are inhibited. Among the modulated miRNA, some are involved in the extracellular matrix:
  The miR-29a and miR-29b, regulators of the expression of COL1A1, COL5A1, of elastin and fibrillin, are increased.
  The miR-22-5p that is associated with the expression of the gene MMP1 is inhibited.

Advantageously according to the invention, an active ingredient that is obtained from the *Calendula officinalis* flowers, applied on the skin, regulates the expression of the miRNA and thus normalizes the expression profile of the SAHF fibroblasts. In particular, it is capable of restoring the genes of the matrix by limiting the expression of miR-29a by 14% and miR-29b by 20% and of reducing the expression of the MMP1 by restoring the expression of miR-22-5p (+18%). It thus preserves the fibrillin and elastin networks and restores the synthesis of procollagen 1.

Thus, via the modulation of miRNA, the use of an active ingredient obtained from *Calendula officinalis* flowers promotes the synthesis of matrix proteins and limits the deleterious effects of aging.

The object of the invention is therefore the use of an active ingredient obtained from *Calendula officinalis* flowers in the prevention or the treatment of cutaneous manifestations caused by imbalances of the expression of miRNA in the skin cells.

In terms of the invention, "cutaneous manifestations caused by an imbalance of the epigenome in the skin cells" or "cutaneous manifestations caused by a modification of the chromatin of the chromosomes of skin cells" or "cutaneous manifestations caused by imbalances of the expression of miRNA in the skin cells" are defined as all manifestations on the skin that are derived from an imbalance of the epigenome in the skin cells/a modification of the chromatin of the chromosomes of the skin cells/of the expression of miRNA in the skin cells, in particular: loss of skin elasticity and tone, modifications of the microrelief of the skin, modification of the surface grain of the skin, signs of cutaneous aging in general.

According to the invention, an active ingredient that is obtained from *Calendula officinalis* flowers can therefore be used on the skin for boosting the epigenome, in particular for regulating the modifications of the chromatin, for preventing the modification of the histones, in particular H3K9 and H2AX, and for regulating the production of miRNA. It thus promotes the synthesis and preserves the matrix proteins; in particular, it normalizes the synthesis of procollagen 1, it preserves the organization of elastin and fibrillin fibers, and it inhibits the expression and the release of MMP1. It therefore makes it possible in particular to combat the deleterious effects of aging, particularly to increase the skin's elasticity and tone, to smooth the microrelief, to improve the homogeneity and the surface grain of the skin, and to impart a more youthful appearance.

According to a particularly suitable embodiment, the active ingredient obtained from the *Calendula officinalis* flowers that is useful according to the invention is an active ingredient that does not contain polyphenols (i.e., containing less than 0.02% by weight of dry material, polyphenol content determined by HPLC), in particular neither rutin-type flavonoids nor terpenes. Preferably, it involves a hydrolyzate of *Calendula officinalis* flowers, particularly a hydrolyzate of *Calendula officinalis* flowers comprising oligosaccharides with a degree of polymerization of between 2 and 10, consisting of fructose and glucose. Even more preferably, it involves an enzymatic hydrolyzate of *Calendula officinalis* flowers.

The object of the invention is also specifically such a hydrolyzate.

In particular, the invention has as its object a hydrolyzate of *Calendula officinalis* flowers comprising oligosaccharides with a degree of polymerization of between 2 and 10, consisting of fructose and glucose. Preferably, the hydrolyzate contains at least 2.5% oligosaccharides with a degree of polymerization of between 2 and 10, consisting of fructose and glucose.

"Hydrolyzate of *Calendula officinalis* flowers" is defined as a set of molecules obtained by hydrolysis of an aqueous solution of *Calendula officinalis* flowers.

The percentages being given by weight relative to the weight of dry materials of the extract.

The hydrolyzate can be a chemical hydrolyzate but in a preferred way, it is an enzymatic hydrolyzate.

In a preferred way, it contains at least 13% of sugars by weight of dry material, in particular at least 20% of sugars by weight of dry material.

According to a suitable embodiment, it comes in liquid form and has at least one of the following characteristics:
  A level of dry material of between 28 and 43 g/l,
  A total sugar content of between 6 and 11 g/l, or between 13% and 40% by weight relative to the dry material, preferably between 21 and 26%.

The level of dry material can be measured by passing a sample with a given initial weight through the oven at 105° C. in the presence of sand until a constant weight is obtained.

The total sugar content can be measured by the DUBOIS method (in the presence of concentrated sulfuric acid and phenol, the reducing sugars provide an orange-yellow compound; from a standard range, it is then possible to determine the carbohydrate level). The glucidic fraction of the hydrolyzate according to the invention primarily consists of monosaccharides and oligosaccharides of fructose and glucose, with a degree of polymerization for the most part of between 1 and 10 (determination of molar masses by HPLC with detection RI and composition of simple sugars determined by ionic liquid chromatography).

The hydrolyzate contains between 0 and 5 µg/ml of polyphenols (content of polyphenols expressed in terms of rutin determined by HPLC, with a quantification limit of 5 µg/ml), or less than 0.02% of polyphenols by weight relative to the dry material.

The hydrolyzate can also contain proteins. The protein fraction preferably consists very heavily of peptides having a molecular weight of less than 2,000 Da (quantification by spectrophotometric metering, Lowry method).

The hydrolyzate according to the invention can be obtained by a process that comprises the series of the following stages:
  Solubilization of powder of *Calendula officinalis* flowers in water,
  Hydrolysis, preferably enzymatic hydrolysis,
  Separation of soluble and insoluble phases, by decanting, filtration, centrifuging,
  Heat treatment for deactivation of enzymatic activity,
  Selective filtration of carbohydrates,
  Concentration and sterilizing filtration.

The parameters of different stages are to be adjusted so as to obtain active ingredients having the characteristics of the invention.

These stages are common in the field of extractions of active ingredients from plants or yeasts, and one skilled in the art is able to adjust the reaction parameters thereof on the basis of his general knowledge.

This invention also covers the cosmetic compositions including a hydrolyzate of *Calendula officinalis* flowers as described above, in different galenical forms, suitable for the administration by cutaneous topical means.

These compositions can come in particular in the form of oil-in-water emulsions, water-in-oil emulsions, multiple emulsions (water/oil/water or oil/water/oil) that can optionally be microemulsions or nanoemulsions, or in the form of solutions, suspensions, hydrodispersions, aqueous gels or powders. They can be more or less fluid and have the appearance of a cream, a lotion, a milk, a serum, an ointment, a gel, a paste or a foam, or in solid form.

It may involve compositions comprising at least 0.5% hydrolyzate of *Calendula officinalis* flowers according to this invention, preferably between 0.5 and 3%.

In addition to the active ingredient, these compositions comprise a physiologically acceptable and preferably cosmetically acceptable medium, i.e., which does not cause unacceptable feelings of discomfort for the user, such as redness, tingling, or prickling.

The compositions according to the invention can contain as adjuvant at least one compound that is selected from among:
  Oils, which can be selected in particular from among the linear or cyclic, volatile or non-volatile silicone oils;
  Waxes, such as ozokerite, polyethylene wax, beeswax, or carnauba wax,
  Silicone elastomers,
  Surfactants, preferably emulsifiers, whether they are non-ionic, anionic, cationic, or amphoteric,
  Co-surfactants, such as linear fatty alcohols,
  Thickeners and/or setting agents,
  Moisturizers, such as polyols like glycerin,
  Organic filters, Inorganic filters,
Dyes, preservatives, bases,
Tightening agents,
Sequestering agents,
Perfumes,
And mixtures thereof, without this list being limiting.

Examples of such adjuvants are cited in particular in the Dictionnaire CTFA (International Cosmetic Ingredient Dictionary and Handbook published by the Personal Care Product Council).

Of course, one skilled in the art will ensure that possible active or non-active complementary compounds and their quantities are selected in such a way that the advantageous properties of the mixture are not, or essentially not, altered by the addition considered.

These compositions are designed in particular to be used for the care of human skin.

In particular, the object of the invention is a cosmetic human skin-care process, designed to combat the effects of cutaneous aging, in particular for increasing the elasticity and tone of the skin and/or for smoothing the microrelief and/or improving the homogeneity and the surface grain of the skin and/or imparting a more youthful appearance. The process consists in applying on the skin a hydrolyzate of *Calendula officinalis* flowers or a composition containing them, preferably at least once per day.

So as to illustrate the cosmetic effects on the skin of an active ingredient obtained from *Calendula officinalis* flowers, the following examples with their test results are presented.

I. EXAMPLES

I. 1. Example 1

Active Ingredient According to the Invention

An example of the process for obtaining an active ingredient according to the invention comprises the implementation of the following stages:
Solubilization of 40 g of powder of *Calendula officinalis* flowers in 1 l of water while being stirred,
Addition of a carbohydrase-type enzyme, while being stirred for 1 hour,
Separation of soluble and insoluble phases by decanting,
Heat treatment for deactivation of enzymatic activity,
Selective filtration of carbohydrates,
Concentration and sterilizing filtration.

The active ingredient that is obtained is a transparent clear liquid that has a dry material of 35.4 g/l and a pH of 5.

It contains 8.02 g/l of proteins, or 23% of dry material, and 7.1 g/l of carbohydrates, or 20% of dry material.

I. 2 Example 2

Active Ingredient According to the Invention

An example of the process for obtaining an active ingredient according to the invention comprises the implementation of the following stages:
Solubilization of 20 g of powder of *Calendula officinalis* flowers in 1 l of water while being stirred,
Addition of a carbohydrase-type enzyme, while being stirred for 4 hours,
Separation of the soluble and insoluble phases by centrifuging,
Heat treatment for deactivation of the enzymatic activity,
Selective filtration of carbohydrates,
Concentration and sterilizing filtration.

The active ingredient that is obtained is a clear liquid that is clear yellow in color and that has a dry material of 36.9 g/l and a pH of 5.

It contains 8.5 g/l of proteins, or 23% of dry material, and 9.6 g/l of carbohydrates, or 26% of dry material.

1.3 Example 3

Use of an Active Ingredient According to the Invention in a Purifying Lotion

| | Lotion | |
|---|---|---|
| A. | Water | Enough to produce 100% |
| | Glycerin | 3% |
| | Dub diol (Stéarinerie Dubois) | 3% |
| | Butylene glycol | 5% |
| | Carbopol Ultrez 20 (Lubrizol) | 0.3% |
| B. | Fluidanov 20X (Seppic) | 1% |
| | DUB zenoate (Stéarinerie Dubois) | 1.5% |
| | Sepimat HBV (Seppic) | 1% |
| C. | Active ingredient - Example 1 | 4% |
| | Preservative | 1% |

The quantities that are indicated are provided in percentage by weight.

This gel, white, shiny opalescent, with a slight odor and flexible texture, has a pH of 5.9.

It allows an easy application, with a quick penetration and a dry finish, and it does not leave an oily feel.

It can be obtained by implementing the following stages:
Mixing A without Carbopol Ultrez 20,
Switching on propeller and gradually adding Carbopol Ultrez 20,
Emulsifying B in A, with a rotor stator at 1,500 rpm,
Adding C,
Allowing it to stir (at 1,200 rpm) until cooling is completed to ensure complete homogenization.

1.4 Example 4

Use of an Active Ingredient According to the Invention in a Nourishing Cream

| | Nourishing Cream | |
|---|---|---|
| A. | Water | Enough to produce 100% |
| | Glycerin | 2% |
| B. | Rice bran wax (Strahl and Pitsch, Inc.) | 0.5% |
| | Phytowax olive (Sophim) | 0.2% |
| | Dub liquid 85 (Stéarinerie Dubois) | 2% |
| | Lanette N (Sidobre/Sinnova) | 1% |
| | Montanov 202 (Seppic) | 3% |
| | IPM (Stéarinerie Dubois) | 2% |
| C. | Sepinov EMT 10 (Seppic) | 1% |
| D. | Active ingredient - Example 2 | 4% |
| | Preservative | 1% |

The quantities that are indicated are provided in percentage by weight.

This white and shiny emulsion has a pH of 6.6.

It allows easy spreading, it melts on the skin, and it offers a quick-penetrating oily feel, with a soft finish.

It can be obtained by implementing the following stages:
Mixing A and heating it in a water bath at 80° C. while being stirred magnetically,
Mixing B and heating it in a water bath at 80° C. while being stirred magnetically,
When A has reached 80° C., adding C off of a heating plate,
Emulsifying B in A, with a rotor stator at 1,800 rpm,
At 30° C., adding D, in the order indicated, with a rotor stator at 1,500 rpm.

II. EVALUATION OF THE COSMETIC EFFECTIVENESS OF AN ACTIVE INGREDIENT ACCORDING TO THE INVENTION

II. A. In-Vitro Tests
A.1—Study of Chromatin Modifications
a) Modeling

The objective of this study is to model the impact of repeated solar irradiation (SSR) on the chromatin in the normal fibroblasts.

This modeling takes place in two stages:
First stage: Obtaining SAHF ("Senescence-Associated Heterochromatin Foci") fibroblasts following treatment by repeated solar irradiation.
Second stage: Study of the modification of histones:
Phosphorylation of histone H2 ($\gamma$H2AX),
Di- and trimethylation of lysine 9 of the histone H3 (H3K9me2/3).

The operating procedure is the following.
On D0, the normal human fibroblasts are inoculated and incubated.
For several days, an induction of the SAHF phenotype is carried out by repeated solar irradiation (SSR) using a "CPS+" solar simulator.
Next, the cells are recovered for carrying out an immunomarking of $\gamma$H2AX and a Western Blot H3K9.
The results that are obtained are presented in Table 1 below:

TABLE 1

Percentage of $\gamma$H2AX positive cells and H3K9me/3 levels in normal and SAHF fibroblasts.

|  | $\gamma$H2AX | | H3K9me2/3 | |
| --- | --- | --- | --- | --- |
|  | Positive Cells (%) | SAHF/Normal Variation (%) | H3K9me2/3 Levels (UA) | SAHF/Normal Variation (%) |
| Normal Fibroblasts | 2.66 |  | 1.18 |  |
| SAHF Fibroblasts | 11.58 | +335% | 4.76 | +303% |

These results show that the repeated solar irradiation on the fibroblasts brings about the acquisition of an SAHF phenotype characterized by chromatin modifications:
Increase of the phosphorylated form of histone H2 ($\gamma$H2AX),
Increase of the di- and trimethylation of lysine 9 of the histone H3 (H3K9me2/3).
b) Effect of an Active Ingredient According to the Invention on the Modification of Histones The objective of this study is to evaluate the capacity of an active ingredient that is obtained from *Calendula officinalis* flowers (active ingredient of Example 2) to limit the chromatin modifications.

For this purpose, the following studies have been done on SAHF fibroblasts:
The phosphorylation of H2AX ($\gamma$H2AX) by immunocytology,
The di- and trimethylation of lysine 9 of the histone H3 by Western Blot (H3K9me2/3).

In addition, the H2AX ($\gamma$H2AX) phosphorylation by immunohistofluorescence has also been studied on skin explants stressed by repeated solar irradiation (SSR).

The operating procedure of the study is described below.
Treatment of the SAHF Fibroblasts
On D0, the normal human fibroblasts are inoculated and incubated.

For several days, an activation of the SAHF phenotype is carried out by repeated solar irradiation (SSR) using a "CPS+" solar simulator. At the end of the irradiation, the cells may or may not be treated with the active ingredient of Example 2 at 0.10%, 0.25% and 0.50% (V/V).

Next, after 24 hours of incubation:
The cells are either fixed for $\gamma$H2AX immunomarking
Or the cells are extracted and frozen awaiting Western Blot H3K9me2/3.

The results that are obtained are presented in Tables 2 and 3 below:

TABLE 2

Effect of an active ingredient according to the invention on the phosphorylation of H2AX of normal and SAHF fibroblasts.

|  | H2AX Phosphorylation Positive Cells (%) | Effectiveness/ SAHF Fibroblasts Control (%) |
| --- | --- | --- |
| Normal Fibroblasts | | |
| Control | 2.66 | |
| Active ingredient obtained from *Calendula officinalis* 0.50% | 2.08 | |
| SAHF Fibroblasts | | |
| Control | 11.58 | |
| Active ingredient obtained from *Calendula officinalis* 0.10% | 8.10 | −30% |
| Active ingredient obtained from *Calendula officinalis* 0.25% | 5.73 | −51% |
| Active ingredient obtained from *Calendula officinalis* 0.50% | 4.77 | −59% |

TABLE 3

Effect of an active ingredient according to the invention on the methylation of lysine 9 of the histone H3 of normal and SAHF fibroblasts.

|  | H3K9me2/3 Levels (UA) | Effectiveness/ SAHF Fibroblasts Control (%) |
| --- | --- | --- |
| Normal Fibroblasts | | |
| Control | 1.18 | |
| Active ingredient obtained from *Calendula officinalis* 0.50% | 1.10 | |
| SAHF Fibroblasts | | |
| Control | 4.76 | |
| Active ingredient obtained from *Calendula officinalis* 0.10% | 3.13 | −34% |

TABLE 3-continued

Effect of an active ingredient according to the
invention on the methylation of lysine 9 of the
histone H3 of normal and SAHF fibroblasts.

|  | H3K9me2/3 Levels (UA) | Effectiveness/ SAHF Fibroblasts Control (%) |
|---|---|---|
| Active ingredient obtained from Calendula officinalis 0.25% | 2.27 | −52% |
| Active ingredient obtained from Calendula officinalis 0.50% | 2.21 | −54% |

Treatment of Human Skin Explants

On D0, punches 8 mm in diameter are produced from human plastic surgery and are kept alive within the culture medium.

For several days, repeated solar irradiation (SSR) is done using a "CPS+" solar simulator for 30 minutes with an intensity of 330 W (or 52 J/cm$^2$). At the end of the irradiation, the explants are treated topically with the active ingredient of Example 1, formulated with 0.25% and 1% (V/V) or with the placebo.

Next, the explants are recovered 24 hours after the last irradiation and are fixed, dehydrated, and enclosed in paraffin. Cuts (4 μm) are made using a microtome, and an immunohistological marking of γH2AX is carried out.

The results that are obtained are presented in Table 4:

TABLE 4

Effect of an active ingredient according to the
invention on the phosphorylation of H2AX on skin
explants stressed by repeated solar irradiation.

|  | H2AX Phosphorylation Positive Cells (%) | Capacity to Limit H2AX Phosphorylation (%) |
|---|---|---|
| Normal Explants | | |
| Control | 0.77 | |
| SSR Explants | | |
| Control | 16.51 | |
| Placebo | 8.88 | 48% |
| Active ingredient obtained from Calendula officinalis 0.25% | 5.01 | 73% |
| Active ingredient obtained from Calendula officinalis 1.00% | 3.66 | 82% |

These different results first of all show (Tables 2 and 3) that tested at 0.50% on SAHF human fibroblasts, an active ingredient according to the invention makes it possible to significantly reduce:

the phosphorylated form of histone H2 by 59% the methylation of lysine 9 of histone 3 by 54%.

These results are confirmed on SSR explants, since the active ingredient according to the invention, tested at 1%, makes it possible to significantly reduce the phosphorylated form of histone H2 by 82%.

Thus, by significantly reducing the phosphorylation of histone H2 and the methylation of histone 3, the active ingredient according to the invention limits the modifications of chromatin induced by aging.

An active ingredient obtained from Calendula officinalis flowers is therefore capable of keeping the chromatin active.

A.2—Study of the Regulation of miRNome a) Modeling

The objective of this study is to characterize an expression profile of miRNA (miRNome) induced by repeated solar irradiation (SSR) on normal human fibroblasts.

So as to be able to target the miRNA involved in the SAHF model (characterization not described), it was necessary to establish a correlation between the transcriptomic profile and the miRNA profile by following the study design below:

First stage: study of the miRNA profile on the SAHF fibroblasts,

Second stage: study of the mRNA profile on these same SAHF fibroblasts,

Third stage: in silico bioinformatic analyses so as to correlate miRNA/mRNA,

Fourth stage: verification and validation by quantitative PCR.

It was possible to demonstrate that 5 miRNA have an influence on the gene expression profile in the model of SAHF fibroblasts.

The SAHF phenotype is characterized by a modification of the miRNome that impacts:

The chromatin: reduction of the expression of miR-199a-5p, with miR-424-5p regulating HDAC11 and EHMT2

The matrix:
  Decrease in the expression of the miR-22-5p regulating MMP1,
  Increase in the expression of miR-29a, with miR-29b regulating Col1A1, Col5A1, and FBN1.

The results of the quantitative PCR on these miRNA and mRNA confirm the studies of the miRNome and transcriptome.

b) Effect of an Active Ingredient According to the Invention on the Regulation of the miRNome The objective of this study is to evaluate the capacity of an active ingredient according to the invention (Example 2) to regulate the miRNome.

For this purpose, the expression of the miRNA involved in the regulation of the extracellular matrix and the chromatin as well as their target genes by quantitative PCR have been studied on SAHF fibroblasts.

The operating procedure is described below.

Treatment of SAHF Fibroblasts

On D0, the normal human fibroblasts are inoculated and incubated.

For several days, an activation of the SAHF phenotype is initiated by repeated solar irradiation (SSR) using a simulator. At the end of the irradiation, the cells may or may not be treated with the active ingredient according to the invention at 0.25% and 0.50% (V/V).

Next, cells are recovered 6 hours after the irradiation: the cells are recovered, and the total RNA (small and large) are extracted.

Quantitative PCR: miRNA

The RNA have been reverse-transcribed, and the complementary DNA obtained have been analyzed by the quantitative PCR technique.

The expression of the miRNA has been studied: miR-199-5p, miR-424-5p, miR-22-5p, miR-29a, miR-29b.

In parallel, the following were analyzed as internal reference controls for normalization: small nucleolar RNA C/D box 68 (SNORD68), small nucleolar RNA C/D box 96A (SNORD96A), RNA U6 small nuclear 2 (RNU6-2).

Quantitative PCR: mRNA

The RNA was reverse-transcribed, and complementary DNA obtained were analyzed by the quantitative PCR technique.

The expression of mRNA was studied: HDAC11, EHMT2, COL1A1, COL5A1, FBN1, MMP1.

In parallel, the mRNA of the ribosomal protein S27 (RPS27), hypoxanthine phosphoribosyltransferase 1 (HPRT1), and beta-glucuronidase (GUSB) were analyzed as internal reference controls for normalization.

The quantification of the incorporation of fluorescence (SYBR Green) is measured continuously using a thermal cycler. The analysis of the Ct (relative quantification) is carried out using software.

The results obtained are presented in Tables 5 to 8 below:

TABLE 5

Effect of an active ingredient according to the invention on the expression of the subregulated miRNA of SAHF fibroblasts.

| | miR-22-5p (%) | miR-22 Expression/Control (%) | miR-424-5p (%) | miR-424 Expression/Control (%) | miR-199a-5p (%) | miR-199 Expression/Control (%) |
|---|---|---|---|---|---|---|
| Normal Fibroblasts | | | | | | |
| Control | 100 | | 100 | | 100 | |
| Active ingredient according to the invention 0.50% | 92 | | 94 | | 105 | |
| SAHF Fibroblasts | | | | | | |
| Control | 79 | | 56 | | 62 | |
| Active ingredient according to the invention 0.25% | 89 | +13% | 71 | +27% | 72 | +16% |

TABLE 5-continued

Effect of an active ingredient according to the invention on the expression of the subregulated miRNA of SAHF fibroblasts.

| | miR-22-5p (%) | miR-22 Expression/Control (%) | miR-424-5p (%) | miR-424 Expression/Control (%) | miR-199a-5p (%) | miR-199 Expression/Control (%) |
|---|---|---|---|---|---|---|
| Active ingredient according to the invention 0.50% | 93 | +18% | 77 | +38% | 81 | +31% |

TABLE 6

Effect of an active ingredient according to the invention on the expression of the subregulated miRNA of SAHF fibroblasts.

| | miR-29a (%) | miR-29a Expression/Control (%) | miR-29b (%) | miR-29b Expression/Control (%) |
|---|---|---|---|---|
| Normal Fibroblasts | | | | |
| Control | 100 | | 100 | |
| Active ingredient according to the invention 0.50% | 105 | | 105 | |
| SAHF Fibroblasts | | | | |
| Control | 117 | | 161 | |
| Active ingredient according to the invention 0.25% | 115 | −2% | 161 | |
| Active ingredient according to the invention 0.50% | 101 | −14% | 129 | −20% |

TABLE 7

Effect of an active ingredient on the expression of the subregulated mRNA of SAHF Fibroblasts

| | Col1A1 (%) | Col1A1 Expression/Control (%) | Col5A1 (%) | Col5A1 Expression/Control (%) | FBN1 (%) | FBN1 Expression/Control (%) |
|---|---|---|---|---|---|---|
| Normal Fibroblasts | | | | | | |
| Control | 100 | | 100 | | 100 | |
| Active ingredient according to the invention 0.50% | 97 | | 91 | | 107 | |
| SAHF Fibroblasts | | | | | | |
| Control | 14 | | 14 | | 24 | |
| Active ingredient according to the invention 0.25% | 18 | +29% | 17 | +21% | 31 | +29% |
| Active ingredient according to the invention 0.50% | 20 | +43% | 19 | +36% | 33 | +38% |

II. B. In-Vivo Tests

B.1—Description of the Selected Panel and In-Vivo Studies

The objective of these studies was to evaluate in vivo the anti-aging effect of the active ingredient according to the invention formulated with 3% in emulsion after 42 days of application on volunteers selected as looking "older than their age" and on whom the impact of the environmental component during their life (evaluated using a questionnaire making it possible to study aspects such as photoexposure, tobacco, eating habits, psycho-social factor . . . ) was most unfavorable.

The signs of aging, which make it possible to distinguish individuals appearing "older than their age" from individuals appearing "younger than their age," have been determined using a previous study conducted on two groups of volunteers: the first group (11 volunteers) corresponding to individuals looking "less than their age", and the second group (15 volunteers) corresponding to individuals looking "more than their age."

Among the parameters studied, those for which significant differences between the two groups have been able to be observed are the following:

|  | Variation of Group Acting Older/Group Acting Younger (%) |
|---|---|
| Characteristic parameters of biomechanical properties of the skin: | Tone: −47.5%<br>Firmness: −7.6%<br>Elasticity: −7.3% |
| Parameters that pertain to the relief of crow's feet and of nasolabial fold: | Crow's feet: +17.5%<br>Nasolabial fold: +44% |
| Parameters involved in the notion of the luminosity of complexion | Skin grain: −15.1%<br>Transparency: −13.9%<br>Radiance: −10.4%<br>Rose color: −17.0%<br>Effect of a good appearance: −12.0% |

The following study was carried out on the active ingredient according to this invention (Example 2) formulated with 3% in emulsion in comparison to a placebo emulsion.

The volunteers selected as "looking older than their age" were divided into two groups in the following manner:

Group A—Placebo: group of 19 volunteers aged between 48 and 62 years (mean age 54±4 years), having applied—morning and evening—the placebo formula on the entire face for 42 days according to the established randomization Group B—Active ingredient: group of 20 volunteers aged between 47 and 60 years (mean age 53±4 years), who applied—morning and evening—the active ingredient according to the invention formulated with 3% in emulsion on the entire face for 42 days according to the established randomization.

The operating procedure of the study is the following.

Between D14 and D0: Twice-daily applications of a placebo cream over the entire face.

On D0:
Taking measurements of biomechanical properties of the skin using a Cutometer® in the area of the cheeks,
Making 3D acquisitions of crow's feet by fringe projection onto crow's feet,
Taking digital photos,
Evaluating the luminosity of complexion by two expert juries.

Between D0 and D41: Twice-daily applications of the placebo or active ingredient according to the invention on the entire face.

On D42:
Taking measurements of biomechanical properties of the skin using a Cutometer® in the area of the cheeks,
Making 3D acquisitions of crow's feet by fringe projection onto crow's feet,
Taking digital photos,
Evaluating the luminosity of complexion by two expert juries.

B.2—Effect of an Active Ingredient According to the Invention on the Biomechanical Properties of the Skin The objective of this study is to evaluate, in vivo, the firming effect of an active ingredient of this invention, in the area of the cheeks, by cutometry, in comparison to a placebo group.

The evaluation of the biomechanical properties of the skin was done before and after 42 days of twice-daily applications of the placebo or the active ingredient using a Cutometer®.

The study of the biomechanical properties of the skin is carried out using a Cutometer® in the area of the cheeks. The skin is sucked into the opening of a probe with a 6 mm diameter by a constant partial vacuum for a constant period. Multiple successive suctioning-in cycles are carried out. The depth of penetration of the skin in the probe is measured by means of two optical prisms placed at the opening of the probe (no friction, no mechanical effect). From the curves obtained, it is possible to calculate various characteristic parameters of the biomechanical properties of the skin. Among the parameters calculated from the curves that are obtained, the elasticity parameter is adopted to quantify the evolution of biomechanical properties in the area of the cheeks:

The firmness of the skin is assessed by the parameter R0:

$$R0 = Uf$$

If −R0 increases, the firmness of the skin is greater.

The elasticity of the skin is assessed by the parameter R5: net elasticity $$R5 = Ur/Ue$$

If R5 increases, the elasticity of the skin increases.

The tone of the skin is assessed by the parameter X: tone or elastic retraction $$X = (Uf - Ur) = R0(1 - R7)$$

If −X increases, the tone increases.

The summary of the results that are obtained is presented in Table 11 below:

TABLE 11

Effect of an active ingredient formulated with 3% in emulsion on the biomechanical properties of the skin in the area of the cheeks. Comparison to the placebo group.

|  | Variation/Placebo (%) |
|---|---|
| Firmness (parameter -R0) | +7.6% |
| Elasticity (parameter R5) | +11.8% |
| Tone (parameter -X) | +12.5% |

It is noted that under the conditions of this study, after 42 days of twice-daily applications and in comparison to a placebo group, the active ingredient according to the invention that is formulated with 3% in emulsion increases significantly:

The parameter −R0, characteristic of the firmness of the skin, of 7.6%. This effect is validated in 90% of the volunteers between D0 and D42.

The parameter R5, characteristic of the elasticity of the skin, of 11.8%. This effect was validated in 90% of the volunteers between D0 and D42.

The parameter −X, characteristic of the tone of the skin, of 12.5%. This effect was validated in 95% of the volunteers between D0 and D42.

B.3—Effect of an Active Ingredient According to the Invention on the Cutaneous Relief of Crow's Feet The objective of the study is to evaluate in vivo the anti-wrinkle effect of an active ingredient according to the invention on the cutaneous relief of the crow's feet by fringe projection, in comparison to a placebo group.

3D acquisitions by fringe projection onto crow's feet were made before and after 42 days of twice-daily treatment of the placebo or the active ingredient.

The acquisitions in the area of the crow's feet were made using a fringe-projection device dedicated to the 3D measurement of the cutaneous relief. This system comprises a measurement sensor combining a light-fringe projector and a high-resolution CCD camera connected to Optocat acquisition software.

A system for repositioning the volunteer's head along the 3 axes of movement makes it possible to find the same measurement zone again at different times during the study.

The effect of the product is measured on an 18×18 mm region of interest that is automatically cut into the original acquisition.

The microrelief of the skin is studied by two 3D roughness parameters

Sq: root mean square of surface roughness.
Sa: route mean square of surface roughness.
The wrinkle volume is studied by a volume parameter
Negative volume: volume of less than the surface of the skin.

A decrease in these various parameters is characteristic of a smoothing of the relief of the surface being studied and a decrease in wrinkles.

A summary of the results that are obtained is presented in the table below:

TABLE 12

Anti-wrinkle effect of an active ingredient according to the invention formulated wtih 3% in comparison to the placebo after 42 days of twice-daily applications. Comparison to the placebo group.

| | Variation/Placebo (%) |
|---|---|
| Parameter Sa | −9.0% |
| Parameter Sq | −8.6% |
| Negative volume | −22.6% |

Under the conditions of this study, after 42 days of twice-daily applications and in comparison to a placebo group, it is noted that an active ingredient obtained from *Calendula* formulated with 3% in emulsion:

Smoothes the cutaneous relief in the area of the crow's feet. Actually, it significantly decreases
  The parameter Sa by −9.0%. This effect was validated in 75% of the volunteers between D0 and D42
  The parameter Sq by −8.6%. This effect was validated in 70% of the volunteers between D0 and D42.
Reduces the wrinkles by allowing a decrease in the negative volume parameter (−22.6%). The study of the distribution of results shows a decrease in the negative volume in 75% of the volunteers between D0 and D42.

B.4—Effect of an Active Ingredient According to the Invention on the Cutaneous Relief of the Nasolabial Fold The objective of the study is to evaluate in vivo the anti-wrinkle effect of an active ingredient according to the invention by visual scoring on digital photographs, in comparison to a placebo group.

Photographs, which make it possible to evaluate the stage of wrinkles of the nasolabial fold, were taken before and after 42 days of twice-daily treatment of the placebo or of an active ingredient according to the invention.

The photographs, which make it possible to evaluate the stage of wrinkles in the area of the nasolabial fold, were taken under lighting and repositioning conditions.

A jury consisting of 3 individuals then evaluated the stage of wrinkles of each photograph of the nasolabial fold on a scoring scale previously defined over 6 stages.

According to the recommendations for the evaluation of the relief of the nasolabial fold are obtained from the Atlas book on aging, vol 1 (Bazin, R., Editions Med'Com). The recommendations for carrying out the evaluation are as follows:

Evaluation of the depth of the fold between the base of the nose and the corner of the lips, corresponding to the <<feature>> at the bottom of the line visible in the photograph.
In the case of double or triple folds, selecting the most significant fold
Evaluating the fold and not the shadow created by the <<bulging>> of the cheek, nor the ptosis of the cheek on the fold.

A decrease in the mean wrinkle stage is characteristic of a reduction of the nasolabial fold.

A summary of the results that are obtained is presented in the table below:

TABLE 13

Effect of an active ingredient formulated with 3% in emulsion on the wrinkle stage of the nasolabial fold evaluated by visual scoring on digital photographs. Comparison to the group with the placebo.

| | Variation/Placebo (%) |
|---|---|
| D 42 | −15.2% |

Under the conditions of this study, after 42 days of twice-daily applications and in comparison to a placebo group, it is noted that an active ingredient obtained from *Calendula officinalis* formulated with 3% in emulsion significantly reduces by 15.2% the mean wrinkle stage in the area of the nasolabial fold after a visual evaluation performed blind on the photographs.

This effect was validated in 55% of the volunteers who participated in this study between D0 and D42.

B.5—Effect of an Active Ingredient According to the Invention on the Luminosity of Complexion The objective of this study is to evaluate, in vivo, the effect of an active ingredient according to the invention on the luminosity of complexion in comparison to a placebo group.

The evaluation of the luminosity of complexion of the face was performed blind, by two experts trained to judge various representative parameters of the luminosity of the complexion, before and after 42 days of twice-daily applications of the placebo or the active ingredient.

The evaluation is done from a scale of scores (from 1 to 10), and the following parameters were adopted:

The skin grain, actually the irregularity of the cutaneous surface, is correlated with the dullness factor of the skin.

The transparency of the skin makes it possible to see the veinlets through the skin. The finer the skin, the more it allows the light to pass, which provides an effect of a good appearance.

A radiant skin is characteristic of a luminous complexion. The greater the intensity of the catchers of light on the projecting zones of the face, the more luminous the skin.

The clear rose color makes it possible to characterize a luminous complexion. The more rosy the complexion, the more fresh it appears.

The general assessment of the effect of a good appearance takes into account the homogeneity of color and its spatial distribution over the entire face.

The evaluation of these various parameters is done on the following areas:
Cheekbones,
Forehead,
Chin,
Eyes.

A summary of the results that are obtained is presented in the table below:

TABLE 14

Effect of an active ingredient according to the invention formulated with 3% in emulsion on the parameters that are characteristic of the brightness of complexion. Comparison to the placebo group.

| | Variation/Placebo (%) |
|---|---|
| Skin grain | +8.3% |
| Transparency | +12.3% |
| Radiance | +10.7% |
| Rose color | +19.7% |
| Effect of a good appearance and good health | +11.5% |

Under the conditions of this study, after 42 days of twice-daily applications and in comparison to a placebo group, an active ingredient according to the invention that is formulated with 3% in emulsion:

Improves the cutaneous microrelief by refining the grain of the skin (+8.3%). This effect was validated in 80% of the volunteers between D0 and D42.

Significantly improves the radiance and transparency parameters of the skin respectively by 10.7% (effect validated in 95% of the volunteers), and by +12.3% (effect validated in 70% of the volunteers) between D0 and D42.

Significantly increases the rose color, characteristic of a fresh complexion, by 19.7% and provides an effect of a good appearance (+11.5%). This effect was validated respectively in 80 and 70% of the volunteers between D0 and D42.

B.6—Effect of an Active Ingredient According to the Invention on the Perception of Age The objective of this study is to evaluate in vivo the effect of the active ingredient according to the invention on the perception of the age of the volunteers by a panel of unbriefed evaluators, in comparison to a placebo group.

Front and profile photographs were taken under standardized conditions before and after 42 days of twice-daily treatment by the placebo or by the active ingredient according to the invention. From these photographs, an evaluation of the perceived age of each volunteer was carried out by a panel of unbriefed evaluators.

TABLE 15

Effect of the active ingredient according to the invention formulated with 3% on the perception of age in comparison to the placebo group after 42 days of twice-daily applications.

| | Perceived Age (Years) | |
|---|---|---|
| | D 0 | D 42 |
| Placebo | 59 | 59 |
| Active ingredient according to the invention 3% | 59 | 56 |

Under the conditions of this study, after 42 days of twice-daily applications and in comparison to the placebo group, the active ingredient according to the invention formulated with 3% in emulsion makes possible a significant improvement of the age perceived by a panel of unbriefed evaluators. All of the subjects who tested the active ingredient according to the invention showed this effect.

The group of volunteers who used the active ingredient according to the invention is perceived, on average, to be younger by 3 years relative to the age attributed to these same volunteers before treatment.

The invention claimed is:

1. A hydrolyzate of *Calendula officinalis* flowers comprising oligosaccharides with a degree of polymerization of between 2 and 10, consisting of fructose and glucose, wherein the hydrolyzate is an enzymatic hydrolyzate, and wherein the hydrolyzate contains neither polyphenols nor terpenes.

2. The hydrolyzate according to claim 1, wherein the hydrolyzate contains at least 2.5% oligosaccharides with a degree of polymerization of between 2 and 10, consisting of fructose and glucose.

3. The hydrolyzate according to claim 1, wherein the hydrolyzate contains at least 13% sugars.

4. A method of boosting the epigenome in skin cells, comprising topically applying on the skin of a subject in need there of an effective amount of an active ingredient obtained from *Calendula officinalis* flowers, wherein the active ingredient is an enzymatic hydrolyzate of *Calendula officinalis* flowers, wherein the active ingredient contains neither polyphenols nor terpenes.

5. The method according to claim 4, wherein boosting the epigenome in the skin cells comprises regulating modifications of chromatin of the skin cells.

6. The method according to claim 5, wherein boosting the epigenome in the skin cells comprises preventing modifications of histones H3K9 and H2AX in the skin cells.

7. The method according to claim 4, wherein boosting the epigenome in the skin cells comprises regulating expression of miRNA in the skin cells.

8. The method according to claim 7, wherein boosting the epigenome in the skin cells comprises regulating expression of miR-29a, miR-29b, miR-22, miR-424, miR-199a in the skin cells.

9. The method according to claim 4, wherein the enzyme hydrolysate comprises oligosaccharides with a degree of polymerization of between 2 and 10, consisting of fructose and glucose.

10. A cosmetic composition, comprising at least 0.5% by weight of dry material of the hydrolyzate according to claim 1.

11. The cosmetic composition according to claim 10, wherein it comprises between 0.5 and 10% by weight of dry material of the hydrolyzate.

12. A cosmetic skin-care process for combating the effects of cutaneous aging, comprising applying on the skin of a subject in need thereof an effective amount of the hydrolyzate according to claim 1 or a cosmetic composition comprising at least 0.5% by weight of dry material of the hydrolyzate.

13. A cosmetic skin-care process for having at least one effect selected from the group consisting of increasing the elasticity and tone of the skin, for smoothing the microrelief, improving the homogeneity and the surface grain of the skin, and imparting a more youthful appearance, comprising applying on the skin of a subject in need thereof an effective amount of the hydrolyzate according to claim 1 or a cosmetic composition comprising at least 0.5% by weight of dry material of the hydrolyzate.

\* \* \* \* \*